(12) United States Patent
Marshall

(10) Patent No.: US 7,189,834 B2
(45) Date of Patent: Mar. 13, 2007

(54) OLIGORIBONUCLEOTIDES ALERT THE IMMUNE SYSTEM OF ANIMALS TO THE IMMINENCE OF MICROBIAL INFECTION

(76) Inventor: William E. Marshall, 155 1st Ave. South, Naples, FL (US) 34102-5946

( * ) Notice: Subject to any disclaimer, the term of this patent is extended or adjusted under 35 U.S.C. 154(b) by 228 days.

(21) Appl. No.: 10/800,926

(22) Filed: Mar. 15, 2004

(65) Prior Publication Data

US 2005/0032731 A1    Feb. 10, 2005

Related U.S. Application Data

(63) Continuation-in-part of application No. 09/883,550, filed on Jun. 18, 2001, which is a continuation of application No. 09/193,653, filed on Nov. 17, 1998, now abandoned, which is a continuation-in-part of application No. 08/739,264, filed on Oct. 29, 1996, now Pat. No. 5,840,318, which is a continuation-in-part of application No. 08/517,016, filed on Aug. 18, 1995, now abandoned, which is a continuation-in-part of application No. 08/376,175, filed on Jan. 20, 1995, now abandoned, which is a continuation-in-part of application No. 08/059,745, filed on May 11, 1993, now abandoned.

(51) Int. Cl.
*C07H 19/00* (2006.01)
(52) U.S. Cl. .................... 536/23.1; 424/278.1
(58) Field of Classification Search ............. 424/278.1; 536/23.1
See application file for complete search history.

(56) References Cited

U.S. PATENT DOCUMENTS

| | | | |
|---|---|---|---|
| 4,314,995 A | 2/1982 | Hata et al. | |
| 4,347,240 A | 8/1982 | Mutai et al. | |
| 4,849,506 A | 7/1989 | Ransom et al. | |
| 4,975,467 A | 12/1990 | Ku et al. | |
| 5,041,427 A | 8/1991 | Takayama et al. | |
| 5,055,447 A | 10/1991 | Palladino et al. | |
| 5,082,657 A | 1/1992 | Ranson | |
| 5,082,838 A | 1/1992 | Naka et al. | |
| 5,151,498 A | 9/1992 | Beuscher et al. | |
| 5,157,039 A | 10/1992 | Nielsen et al. | |
| 5,158,939 A | 10/1992 | Takayama et al. | |
| 5,413,785 A | 5/1995 | Nanji | |
| 5,840,318 A | 11/1998 | Marshall et al. | |
| 6,239,116 B1 * | 5/2001 | Krieg et al. | ............... 514/44 |

FOREIGN PATENT DOCUMENTS

WO    WO 9837919 A1 *    9/1998
WO    WO 200122972 A2 *    4/2001

OTHER PUBLICATIONS

Perdigon et al., J. Food Protection, 53:404-410 (May 1990).

* cited by examiner

*Primary Examiner*—Robert A. Zeman
(74) *Attorney, Agent, or Firm*—McKee, Voorhees & Sease, P.L.C.

(57) ABSTRACT

This invention provides novel methods and compositions for modulating and stimulating the immune system of animals to withstand microbial infections and the lethality of endotoxic shock by feeding or injecting bacteria-free oligoribonucleotides (ORNs) released by either harmless or pathogenic bacteria. The invention also describes the molecular mode of action of the health benefits derived from consuming fermented dairy products and probiotic bacteria.

2 Claims, 2 Drawing Sheets

SEQUENCE LISTING

<160> NUMBER OF SEQ ID NOS: 3

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence: Synthetic
      oligoribonucleotide

<400> SEQUENCE: 1
agagggucgc acgcggua                                                 18

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Synthetic
      oligoribonucleotide

<400> SEQUENCE: 2
cguacugcaa cucg                                                     14

<210> SEQ ID NO 3
<211> LENGTH: 20
<212> TYPE: RNA
<213> ORGANISM: Artificial Sequence
<220> FEATURE:

-continued

```
<223> OTHER INFORMATION: Description of Artificial Sequence: Synthetic
      oligoribonucleotide

<400> SEQUENCE: 3
agguacagcc aggacuacga                                                    20
```

OLIGORIBONUCLEOTIDES ALERT THE IMMUNE SYSTEM OF ANIMALS TO THE IMMINENCE OF MICROBIAL INFECTION

CROSS-REFERENCE TO RELATED APPLICATIONS

This application is a continuation-in-part that claims the benefit of priority under 35 U.S.C. § 120, to copending application Ser. No. 09/883,550 filed on Jun. 18, 2001, which is a continuation of Ser. No. 08/739,264 filed Oct. 29, 1996 now U.S. Pat. No. 5,840,318, which is a continuation-in-part of Ser. No. 08/517,016 filed Aug. 18, 1995 now abandoned, which is a continuation-in-part of Ser. No. 08/376,175 filed Jan. 20, 1995 now abandoned, which is a continuation-in-part of Ser. No. 08/059,745 filed May 11, 1993 now abandoned and is also a continuation-in-part that claims the benefit of priority under 35 U.S.C. § 120, of application Ser. No. 09/429,199 filed on Oct. 28, 1999 now U.S. Pat. No. 6,589,771 B1, the contents of which are hereby incorporated by reference in their entirety.

FIELD OF THE INVENTION

The present invention relates to methods and compositions for modulating and stimulating the immune system of animals or humans to withstand microbial infections and the lethality of endotoxic shock. In particular, the invention relates to methods of modulating and stimulating the immune response of animals or humans by feeding or by injecting effective amounts of bacteria-free oligoribonucleotides released by either harmless or pathogenic bacteria. The present invention further provides that oligoribonucleotides provide the molecular mode of action to explain the health benefits derived from consuming fermented dairy products and probiotic bacteria.

BACKGROUND

Microorganisms commonly encounter threatening changes in their environments. These changes include depletion of nutrients, shifts in pH, temperature and pressure, and sharing habitats with invading organisms. A commonly encountered stress of animal-associated bacteria and one of importance to a study of infectious diseases is that induced through the transfer of cultures from their propagation media into different media. This stress is especially pronounced when the bacteria are transferred to a media of neutral pH with altered or reduced levels of nutrients, such as when exogenous bacteria enter an animal or when endogenous bacteria penetrate sterile zones and tissues from their non-sterile habitats. During growth, bacteria form H+ which accumulate in both the cell and the media.

When encountering normal and naturally-occurring stresses, bacteria release products known as stress response factors, (SRFs). These SRFs include polymers of nucleic acids and their partial and complete hydrolysates including a mixture of about a dozen oligoribonucleotides (ORNs) ranging from 1–30 nucleotides, which are resistant to further hydrolysis by RNAse.

The present invention has found that a series of mild stresses, mimicking those commonly experienced when bacterial environments change, induces the release of oligoribonucleotides. Their release does not kill or injure the bacteria, but rather assists them in establishing a colony in a new environment by increasing their rate of mutation and their rate of growth.

These oligoribonucleotides are released when bacteria enter the pH neutral environment of animals, such as the mouth, nose, oropharyngeal cavity, urethra and vagina.

Through co-evolution, the immune system of animals and humans has adapted a protective response to the appearance of oligoribonucleotides in anticipation of a microbial invasion. This immune reaction is important when oligoribonucleotides (ORNs) are released by bacteria entering the pH neutral body fluids or attempt to invade horizontally onto sterile tissue, (e.g. from the nose to the sinus, from vagina to uterus). Encountering neutral pH will induce the release of these bacterial factors, which will serve to alert the host to a potential penetration onto a sterile area or into sterile tissue. This immune response involves the stimulation of monocytes and macrophages, sentinel cells embedded in oral pharyngeal tissues as well as the B- and T-cells of the immune system.

Specifically, the macrophage has adapted a preemptory reaction to the presence of the oligoribonucleotides (ORNs) that prepares the immune system to defend the host against infection. For example, when ingested bacteria encounter neutral pH or are overcrowded by the presence of growing pathogens, they will release readily absorbable, non-toxic ORNs which activate tissue macrophages to release Interleukin-1, IL-1, Interleukin-6, IL-6 and Tumor Necrosis Factor, alpha, TNFα which stimulate other cells of the immune system. After being highly activated, exposed macrophages down-regulate the surface receptors, CD-14 and CD-16, thereby desensitizing the cell from over-activation by the subsequent interaction with bacterial toxins if infection occurs.

The present inventor has found that the oligomeric fraction having a molecular weight <10 kDa and, in particular, between 500 and 3,000 Da are readily absorbed, are non-toxic, and both activate and modulate the immune system. The products less than 10 kDa in size are non-toxic and contain further a group of compounds of oligomeric size, i.e. 0.5 to 10 kDa that activate and modulate macrophages. Macrophages are activated to release cytokines at levels deemed helpful to combating infections and are down-modulated to prevent their over-activation with the subsequent release of host-threatening levels of cytokines and becoming overly cytotoxic resulting in perforation of organs.

As sentry cells, macrophages circulate in the blood and lymph as well as reside in specialized endothelial tissues and organs. They are among the host's first lines of defense, releasing interleukin signals, destroying microbes and stimulating other immune cells to destroy diseased cells of the host. Approximately twenty different interleukins can be released modifying, amplifying, restricting and dampening messages as the system is stimulated. Thus, the macrophage's signal is key to initiating and enforcing the appropriate immune response. In an infection, bacterial endotoxin (lipopolysaccharide, LPS), binds to the TOLL-like receptor, TLR-4 and the CD-16 surface molecules on macrophages stimulating them and inducing the release of yet higher levels and combinations of IL-1, IL-6 and TNF. These signals, in turn, induce fever, fatigue, cardiovascular hypotension, renal failure and can dictate the death of the host in "septic shock".

By down-regulating the numbers of CD-14 and CD-16 receptors on the surface of the macrophage, the oligomers released by high levels of stressed bacteria help to ensure that the macrophage does not become over-activated by interleukins thereby creating a system which may go awry killing the host.

Monocytes also respond to the presence of released bacterial ORNs by escaping apoptosis and maturing into macrophages.

Thirteen different species of animal-associated bacteria have been found to release oligoribonucleotides <10 kDa when stressed. However, the distribution of polymer:oligomer:monomer is not equal amongst these species. The levels of ORNs accumulated and released are related to the rate of growth of the bacteria. Therefore, not all strains of bacteria, even of the same species, release levels of oligomers sufficient to protect animals against a subsequent bacterial invasion. An additional discovery is the finding that feral colonies of bacteria yield more oligoribonucleotides (ORNs) when initially stressed than non-feral or laboratory strains. However, inducing a stress upon a laboratory strain before repropagation will stimulate its growth rate and accumulation of ORNs, comparable to that occurring when a feral strain was stressed.

The polymeric fraction (>10 kDa) is toxic when injected into mice, producing a ruffled fur coat, huddling and diarrhea. In vitro assays using human peripheral blood macrophages indicate that the monomeric fraction, (0.5 kDa) does not induce the release of significant levels of interleukins. However, the oligomeric fraction, (between 0.5 and 10. kDa) activates and modulates macrophages, is non-toxic when injected into mice and protects them against a subsequent lethal challenge of injected endotoxin.

The present invention has found that the oligoribonucleotides (ORNs), (between 0.3 and 10. kDa) are a rich new source of natural, normally-occurring, co-evolutionarily evolved immune modulators that can be safely used to protect animals and humans from infections and overstimulation of their immune system. In addition, this fraction contains compounds that can be used to adjust the expression of individual surface receptors on macrophages to re-center a dysfunctional immune system.

Furthermore, in vitro and in vivo testing indicates the potential role as adjuvants of ORNs <10 kDa by stimulating the production of antibodies. Human B-cells were stimulated in cell culture and mice demonstrated increased B-cell activity when an experimental vaccine against melanoma was injected with ORN<10 kDa.

An unusual feature of the ORNs<10 kDa that possess immune stimulating capacity is their resistance to hydrolysis by RNase (product R-7003 purchased from Sigma Chemical Co.) when used as directed by the manufacturer (incubating 750 µL of ORNs with 50 µg of RNase at 37° C. for 3 hr). The pattern of the ORNs<10 kDa on Sephadex G-10 was the same before and after RNase treatment showing no further reduction in molecular size.

The resistance of ORNs<10 kDa to RNase suggests that the ORNs have unusual structures. Some may have substitutions on their bases (e.g., methyl and other groups) or may have two nucleotide strands held together by complementarity or folded back upon themselves. These unusual structural conditions leading to resistance to RNase are believed to be responsible for their stimulation and modulation of the immune system.

In addition to these unusual structures, the inventor believes that the immune system has also learned through co-evolution to recognize the source of the ORNs<10 kDa by certain features that are unique to the source cell or found to occur at frequencies much higher in one type of cell (e.g., bacteria) than in another (e.g., fungi, animals, etc.). That is to say, the immune system has learned that certain structures reveal the nature of the cellular sources of the ORNs<10 kDa. Two examples of structures specific to microbes are known.

The first are the "signature sequences" of nucleotides known to occur uniquely in the ribosomes of specific orders, families, genera or species of microbes. (Woese, CR, 1998, The Universal Ancestor, Proc Natl Acad Sci 95:6854–9, Olsen, G. J, Woese, C. R, Ribosomal RNA: A Key to Phylogeny, FASEB J. 1993 January; 7(1):113–2, and Zhang, K., Willson, R. C., and Fox, G. E., 2002 Bioinformatics 18(2):244–50 Identification of Characteristic Oligonucleotides in the Bacterial 16S Ribosomal RNA Dataset).

The second are the sequences of nucleotides in DNA that contain the CpG motif in DNA at a much higher frequency in bacteria. Injecting oligodeoxynucleotides (ODN), 4 to 10 nucleotides in length, which contain one or two CpG motifs, have been found to stimulate an immune response. However, they are toxic. (Kreig, A M, et al., 1995, CpG Motifs in Bacterial DNA Trigger Direct B-cell Activation, Nature 374: 546–9).

The inventor believes that the immune system recognizes the ribosomal counterparts of these CpG ODNs as being derived from bacteria. However, through co-evolution, it has adapted a non-toxic, alerting response to their sudden release by invading bacteria.

However <10 kDa ORNs collected from heat-killed bacteria stimulate monocytes as well as those from live bacteria but do not protect mice from endotoxic death. Therefore the Mangan assay previously depended upon cannot be relied upon to predict the results of feeding ORNs to animals. (Mangan D F, Welch G R, Wahl S M, 1991, Lipopolysaccharide, tumor necrosis factor-α, and IL-1B prevent programmed cell death (apoptosis) in human peripheral blood monocytes, J Immunol 146:1541–6).

The discovery of the release of immune-activating and modulating factors has broad implications to improving the immune response through diets and pharmaceutical preparations for humans and animals. Products, (e.g. milk, cheese, yogurts) contain viable bacteria, which, when transferred to the nutrient deprived environment of pH neutral body fluids, such as the mouth, release ORNs. If such products were formulated to extend the dwell-time in the mouth and throat, more ORNs would be released, activating and modulating a greater immune response. Likewise, gels used to administer probiotics would deliver more ORNs if the pH of the gel were buffered to neutral pH rather than acidic.

Numerous patents teach the healthful benefits of administering specific viable bacteria to humans and animals either orally or parenterally to provide local immune stimulation. Additionally, the prior art recognizes the importance of modulating interleukin release but does not teach the use of safe, natural, normally occurring products derived from co-evolution, which are effective when taken orally. However, the present invention teaches the administration of sterile, stable, controlled doses of the active principle, ORNs, rather than unstable, viable microorganisms.

U.S. Pat. No. 4,975,467 teaches methods by which synthetic compounds can be used to inhibit the release of IL-1 thereby alleviating the induction of its pathophysiologic conditions. U.S. Pat. No. 5,055,447 provides methods and compositions for the prevention of septic shock by administering growth factor-β. This patent teaches the use of administering a signal compound to intercept or modify existing signals. U.S. Pat. Nos. 5,041,427 and 5,158,939 teach the use of a non-toxic LPS from *R. spaeroides*, ATCC 17023 to desensitize macrophages to toxic LPS. Since *R. spaeroides* has an unusual lipid A structure, it may not be effective as a desensitizing agent. U.S. Pat. No. 5,157,039 supports the clinical importance for controlling IL-1 release by macrophages by teaching the use of two non-natural quinolinol compounds, which appear to be non-selective in IL inhibition. U.S. Pat. No. 5,840,318 teaches that bacteria exposed to a neutral pH buffer for 10–16 hours release compounds <10 kDa in size having a UV maximum absorption at 254 nm. Feeding the <10 kDa sizes activates and modulates an animal's immune system, thereby protecting it against a subsequent lethal challenge of endotoxin. The accumulation of A-254 absorbing compounds is associated with the slowing or termination of bacterial cell growth. Further, U.S. Pat. No. 6,589,771 B1 teaches that bacteria enter dormancy during their stationary phase by accumulating solutes that increase the osmolality and H+ that decrease the intracellular pH of the cell. Putting dormant cells in buffers with osmolalities and hydrogen ion concentrations lower than that of the cell will cause the diffusion of solutes and H+ thereby inducing the arousal of the cell. Rather than a single 10–16 hour wash to induce the release of the compounds that have a maximum of UV absorption at 254 nm, one can employ a series of 20-minute washings in a buffer of pH 7 and of lower osmolality followed by an adjustment period of approximately 72 hours in the final wash.

Livestock are routinely fed silage, a fermented product containing high levels of viable harmless bacteria. When ingested and chewed as cud, the silage bacteria release immune-activating ORNs. The proper selection of harmless bacteria that ferment silage and grains and also release significant levels of ORNs will help improve the health of livestock.

Direct-fed microbials and probiotics are harmless bacteria which are grown in a rich media, concentrated, dried and fed to animals either as a powder for top-dressing or in gel forms for oral inoculation. These products provide a health benefit to the animal in combating infections relating to shipping and weaning. Analysis of commercial products indicates the presence of ORNs as well as the release of ORNs when transferred to saliva or to a nutrient-reduced environment. It is believed the presence and release of ORNs explains their effectiveness. This discovery permits the administration of a sterile, stable, probiotic of known dose for livestock and poultry. Currently, viability of probiotics is believed necessary for effectiveness. A sterile, stable product allows distribution without refrigeration and would provide a known dose.

The present inventor has now found that the extrusion of ORNs from the cell is induced when cells are exposed to neutral aqueous environments, e.g. saliva, body fluids and physiologic saline. Extrusion can be induced by subjecting the bacterial populations to repeated dilutions or washings, as many as 6, in pH neutral buffers of sufficient molarity to offset the efflux of H+ that accompany ORNs. Further, they have discovered doses of ORNs that are also effective in rescuing monocytes from apoptosis and, in addition, rescue animals from the lethality of endotoxemia. Moreover, lab tests have been developed which aid in the selection and screening of bacteria which release the more potent ORNs and determining appropriate doses.

It is therefore an object of this invention is to provide a method to capture the accumulated ORNs released when bacteria enter a pH neutral buffer and administer a sufficient quantity of bacteria-free <10 kDa to animals for the purpose of stimulating an immune response that protects against subsequent microbial infections.

A further object of this invention is to provide oral pharmaceutical compositions to help prevent microbial infections in animals.

Another object of this invention is to provide parenteral injections of individual components of these pharmaceutical compositions to treat endotoxic shock.

A further object of this invention is to provide topical pharmaceutical compositions for the activation and modulation of local immune systems to protect against ear, nose and vaginal infections.

An additional object of this invention is to use individual components of these pharmaceutical compositions as adjuvants in conjunction with vaccination.

A further object of this invention is to provide pharmaceutical compositions to down regulate the cytotoxicity of macrophages and prevent their destruction of normal T-cells in persons suffering from HIV infections.

It is still a further object of this invention to provide ORNs to extend the viability of monocytes, thereby improving their ability to mature into macrophages to fight infection.

It a further object of this invention to provide methods to ensure that bacteria will accumulate and release higher levels and more potent ORNs.

These and other objectives will become apparent from the following detailed description of the invention. It is to be understood that both the foregoing general description and the following detailed description are exemplary and explanatory only and are not restrictive of the invention, as claimed.

SUMMARY

The present invention describes pharmaceutical compositions and methods of use of the same for modulating and stimulating the immune responses in animals. Through the application of a chemical, physical, or biological stress, bacteria release accumulated oligoribonucleotides (ORNs). These ORNs are filtered to remove those larger than 10 kDa. The <10 kDa fraction is then administered to animals to bolster their immune response. The current invention teaches that both harmless and harmful bacteria accumulate ORNs as their exponential growth slows and must extrude or release them to restart growth. Rapidly growing bacteria are a richer source of ORNs than slow-growing ones. Through co-evolution the immune system has adapted an alert response in preparation of an ensuing microbial invasion.

According to a preferred embodiment, the administration of ORNs <10 kDa modulate and stimulate circulating macrophages and monocytes to stimulate the animal's immune system. The accumulated ORNs released when bacteria enter a pH neutral buffer may be extruded by subjecting bacterial populations to repeated dilutions or washings, as many as 6, in pH neutral buffers of sufficient molarity to offset the efflux of H+ that accompany ORNs. By feeding or injecting the non-toxic fraction of <10 kDa this invention demonstrates that the alert response protects animals from the lethality of a subsequent injection of endotoxin. The invention also includes methods and tests to guide in the selection of bacterial strains and stresses to ensure the release of the most effective levels of immune-stimulating ORNs.

DEFINITIONS

For purposes of this application the following terms shall have the definitions recited herein. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUM Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

The term "<10 kDa" refers to substances that are sufficiently small to pass through a molecular filter designed to retain molecules larger than 10,000 Daltons.

The term "<10 kDa ORNs" refers to oligoribonucleotides resulting from the hydrolyses of the ribonucleic acids found in bacterial ribosomes.

The term "arousing" as used herein includes causing dormant cells to revert to their vegetative states. The vegetative state is marked by its ability to propagate in broths or an agar media developed for their growth and identification during the time period allotted the visible observation of colonies (2–3 days) with the naked eye.

As used herein, "CpG ORNs<10 kDa" shall mean oligoribosomal nucleotides that contain the CpG motif. These sequences have been shown to occur in DNA at a much higher frequency in bacteria than in animals. Injecting oligodeoxynucleotides (ODN), 4 to 10 nucleotides in length, which contain one or two CpG motifs has been found to stimulate an immune response. However, they are toxic. (Kreig, A M, et al., 1995, CpG Motifs in Bacterial DNA Trigger Direct B-cell Activation, Nature 374: 546–9). Feeding their counterparts as ribosomal nucleotides will be stimulating and not toxic.

The term "dormant" bacteria as used herein includes (a) bacterial cells that are "viable but not culturable" or "quiescent" or "nascent" or "planktonic" which are (b) metabolically active, but (c) do not propagate in broths or on agar media formulated for their growth and identification during the time period allotted for the observation of colonies (2–3 days) with the naked eye.

The term "endotoxic shock" or "septic shock" includes without limitation a physical or mental disturbance induced by the release of endotoxin from Gram-negative bacteria or by the release of super antigens from Gram-positive bacteria.

The term "hypermutative" cells are those that display the ability to mutate at rates much higher than normal colonies exhibiting polymorphism and changes in antibiotic susceptibilities. As used herein, depicts changes in the characteristics of bacteria that have been subjected to 2–6 serial stresses of washing in pH neutral buffers.

The present invention concerns the preparation and use of "immunopotentiation" agents, whether used alone as a direct immunopotentiation agent, or combined with other compounds, either covalently or simply admixed in the same composition. In the context of the present invention, the term immunpotentiation agent is intended to include immunopotentiating antibodies, as well as certain bacterial proteins which have been determined to have profound immunopotentiation actions.

The term "microbe" refers to any organism too small to be visible to the naked eye and includes bacteria, fungi, protozoa and viruses.

As used herein, the phrase "modulating an immune response in animals" includes: (a) stimulating an immune response by activating macrophages to release immune stimulating interleukins IL-1, IL-6 and TNF (for example to prevent or combat infections); (b) down-regulating the CD-14 and CD-16 receptors of macrophages to prevent over-stimulation by endotoxin leading to the over-production of IL-1, IL-6 and TNF, associated with systemic inflammation, cardiovascular dysfunction, shock and death; (c) down-regulating the CD-16 receptor of macrophages to prevent over-stimulation by IL-10 leading to the over-conversion of macrophages to their cytotoxic phenotype with its potential for excessive destruction of host cells, e.g. endothelial cells lining blood vessels and T-cells; (d) rescuing monocytes from apoptosis; and (e) rescuing animals from the lethality of an endotoxic challenge.

As used herein, the term "pathogenic challenge" describes any virus, microorganism or other substance causing disease or abnormality as would be understood by those ordinarily skilled in the art.

As used herein, the term "pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

As used herein, "pharmaceutically acceptable equivalent" includes, without limitation, pharmaceutically acceptable salts, hydrates, metabolites, prodrugs and isosteres. Many pharmaceutically acceptable equivalents are expected to have the same or similar in vitro or in vivo activity as the compounds of the invention.

As used herein, the terms "pharmaceutically effective" or "therapeutically effective" shall mean an amount of each active component of the pharmaceutical composition (i.e. oligoribonucleotides (ORNs)<10 kDa) or method that is sufficient to show a meaningful patient benefit, i.e., treatment, prevention, amelioration, or a decrease in the frequency of the condition or symptom being treated, to block the effect of the ORNs as determined by the methods and protocols disclosed herein. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the terms "signature Sequences of ORNs<10 kDa" shall mean oligoribosomal nucleotides that contain sequences found only in the ribosomes of specific orders, families, genera or species of microbes. (Woese, CR, 1998, The Universal Ancestor, Proc Natl Acad Sci 95:6854–9, Olsen, G. J, Woese, C. R, Ribosomal RNA: A Key to Phylogeny, FASEB J. 1993 January; 7(1):113–2, and Zhang, K., Willson, R. C., and Fox, G. E., 2002 Bioinformatics 18(2):244–50 Identification of Characteristic Oligonucleotides in the Bacterial 16S Ribosomal RNA Dataset).

As used herein, unless otherwise defined in conjunction with specific diseases or disorders, "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

The term "vegetative" form of dormant bacteria, as used herein, is that form of the bacterial cell from which the dormant cell was formed and reverts to, after arousal and can grow on appropriate media within the limits of times imposed by accepted standard methods (2–3 days).

A known standard of free uracil eluted at 20–25 ml, corresponding to Peak III. Furthermore, thin layer chromatography of Peak III in two different solvents had the same $R_f$ value as free uracil (see Example 9). Peaks II and IV were most likely tetra-, tri-, di- and mononucleotides.

Figure 1:
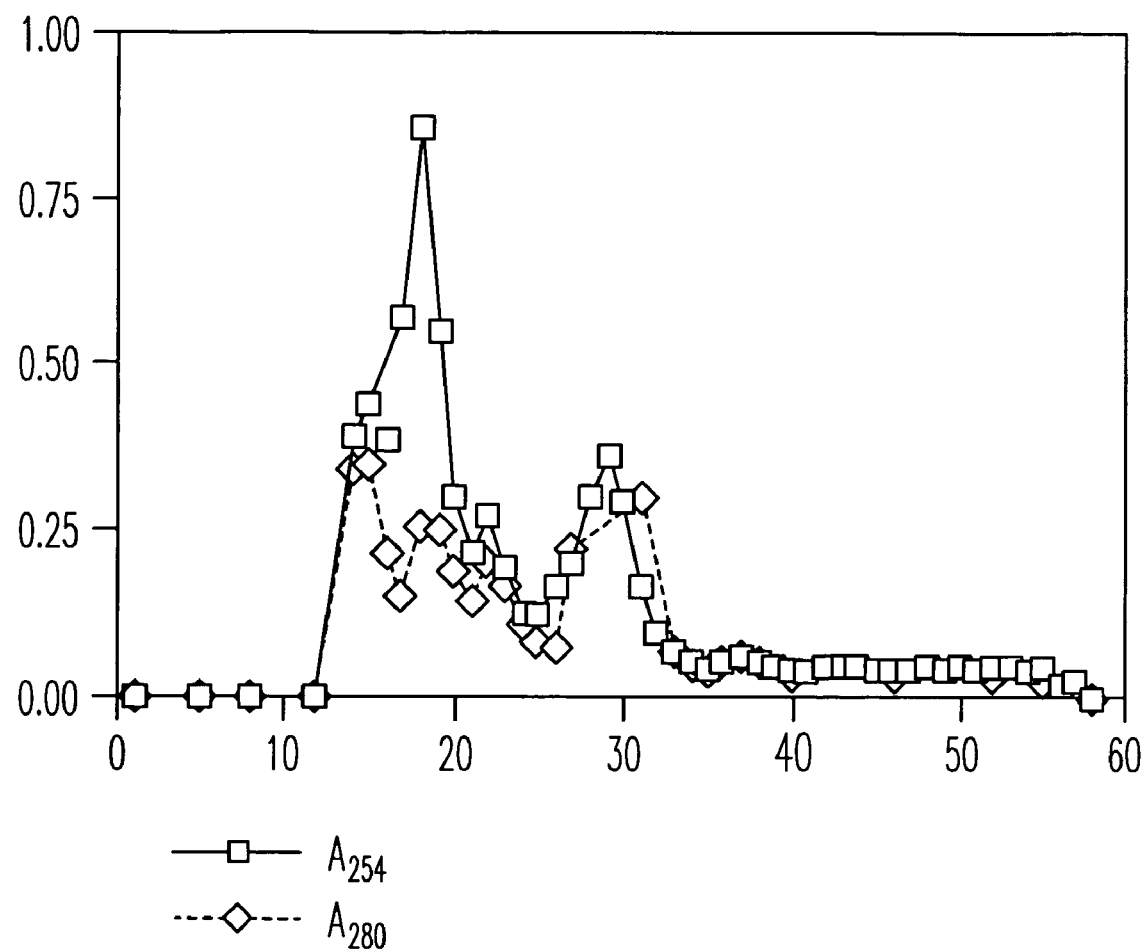
FIG. 1 illustrates the distribution of the molecular sizes of the <10 kDa ORNs released by exposing harmless or pathogenic bacteria to 0.1M phosphate buffered saline, pH 7.3 on a Sephadex G-10 column. Since the average molecular weight of a monoribonucleotide is about 309 or 0.3 kDa, a mixture of ORNs<10 kDa may contain oligonucleotides containing as many as 33 nucleotide units. Slightly less than half of the ORNs eluted at the void volume (Peak I) indicating a size excluded by the void volume of Sephadex G-10, or approximately 1 kDa.
Figure 2:
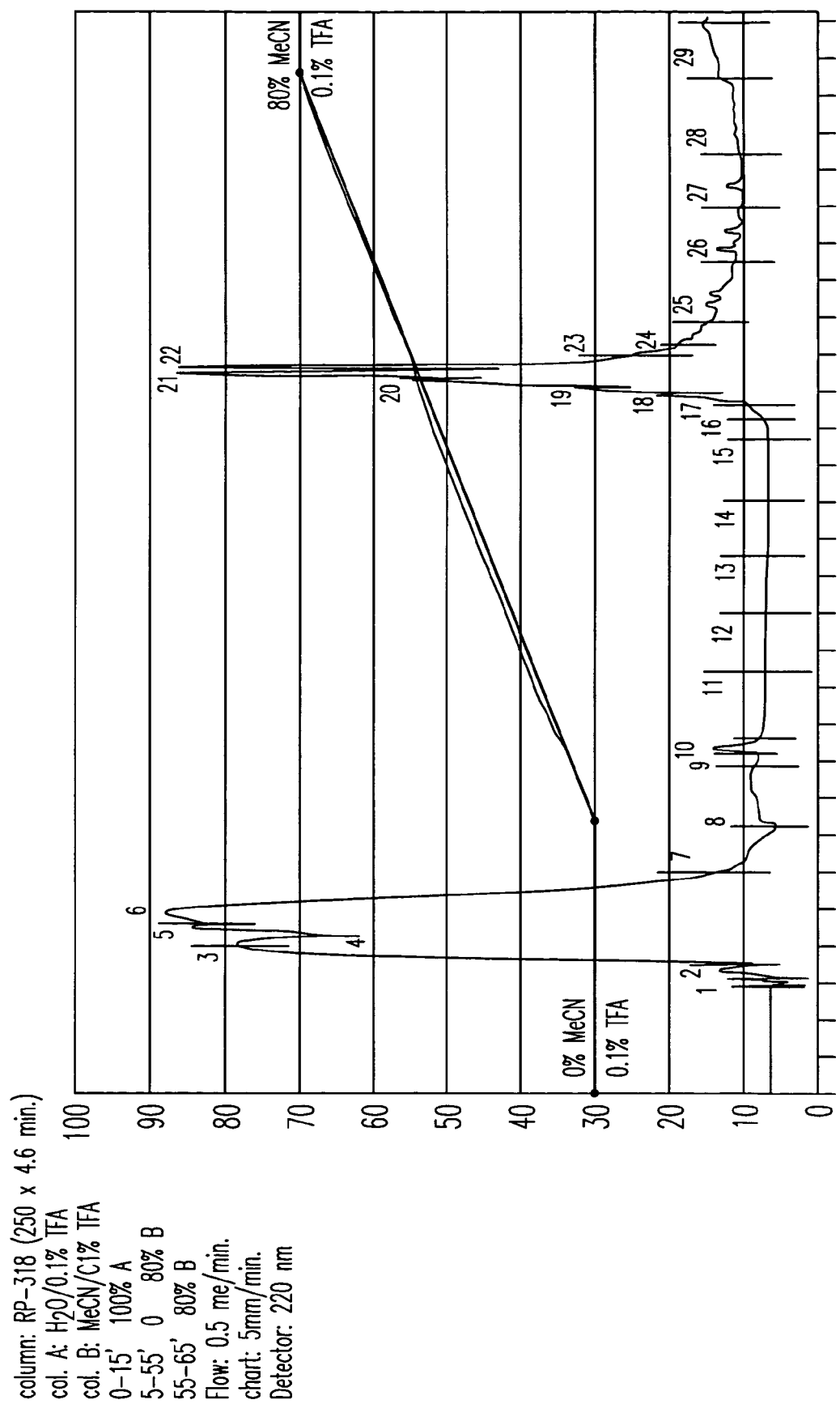

FIG. 2 demonstrates the sample chromatographed by HPLC of the ORNs<10 kDa released by *L. monocytogenes* in a single 20 min. washing in 0.1M PBS, pH 7.3. The figure is an instrument tracing at 220 nm of ORNs separated by HPLC which indicates the presence of two groups, one hydrophobic and one hydrophilic of approximately 6 ORNs in each. The hydrophobic <10 kDa ORNs could be as large as 30-mers while the smaller hydrophilic ones are likely to be the tetra-, tri-, di- and mononucleotides and free uracil observed separated on Sephadex G-10 shown in FIG. 1.

The column was an RP-318, 250 cm×4.6 mm. A 2-solvent system was used to elute the ORNs: 0.1% trifluoroacetate, and 80% methyl cyanide in 0.1% trifluoroacetate. The hydrophilic compounds were eluted 7 min after the flow of 0.1% trifluoroacetate was started. The hydrophobic group was eluted 38 min after the start of the second solvent of 80% methyl cyanide in 0.1% trifluoracetate solvent. The presence of the compounds was detected by absorption at 220 nm.

DESCRIPTION OF THE INVENTION

As set forth above, this invention relates to the production of ORNs in bacteria and the administration of these ORNs in animals to modulate their immune response. The present invention relates to methods and compositions for modulating and stimulating the immune system of animals or humans to withstand microbial infections and the lethality of endotoxic shock. In particular, the invention relates to methods of modulating and stimulating the immune response of animals or humans by feeding or by injection of effective amounts of bacteria-free oligoribonucleotides released by either harmless or pathogenic bacteria is effective.

It has been known since 1958 that the number of ribosomes per bacterial cell reflects the growth rate of the cell, (Physiology of the Bacterial Cell, Neidhardt, F. C., Ingraham, J. L., and Schaechter, M., Sinauer Assoc., Sundrland, Mass., 1990, p. 422). This is a logical relationship since ribosomes are the "factories" of the cell, translating messenger RNA (mRNA) into proteins. Rapidly growing bacteria can have as many as 70,000 ribosomes while cells in stationary phase have 2,000. Ribosomes consist of 57 proteins and 3 rRNA molecules (5S, 16S and 23S) and disappear as the cell population reaches its maximum density, (Davis, B. R., S. M. Luger, and P. C. Tai. 1986. Role of ribosome degradation in the death of starved *E. coli* cells. J. Bact. 166:439–45).

It is currently believed that the loss of ribosomes forces the slowing of cell growth. Surprisingly, the present invention discovers that the slowing of cell replication is accompanied not only by the loss of ribosomes but also by the accumulation of fragments of rRNA. Thus, the invention establishes that the cell has a dual braking system including the loss of ribosomes and the accumulation of oligoribonucleotides (ORNs).

The inventor has discovered that ribosomal RNA is the source of the oligoribonucleotides (ORNs); destruction of the ribosomes begins half way through the exponential growth phase. ORNs start to accumulate in the cytoplasm of the cell as rRNA is hydrolyzed; their association with the genome reversibly denatures DNA, which explains the lag period observed when older cells are transferred into pH neutral fresh media. The cell cannot restart growth until the ORNs have been disassociated from DNA. As bacteria mature through their stationary phase, ORNs continue to associate with DNA extending the lag period into deep dormancy, marked by the cell's resistance to antibiotics and pasteurization. However, only one cell in every 500 successfully enters and exits dormancy; the vast majority accumulates ORNs improperly, leading to irreversible denaturation and death.

It is possible that the bacterial ORNs<10 kDa contain sequences of ORNs that are associated with regions of rRNA that contain ' signature sequences:—a series of nucleotides unique to that family, genus or species. By recognizing their presence the sentry cells may be able to mount a response tailored to that microbe.

In addition, ORNs may be released from the ribosomes of diseased or infected cells belonging to the host, which may also contain sequences unique to the animal as well as to its various tissues and organs. In their response to the sudden appearance of ORNs the host's sentry cell may have developed a number of different, but appropriate responses.

Under optimum conditions of growth, one bacterial cell will pass through 30 generations to form 1–3 billion cells. It has been known since 1909 that cells older than about 12 hours will "lag" four to seven hours before restarting growth when transferred into fresh media (Lane-Clayton, J., 1909, Multiplication of Bacteria and The Influence of Temperature and Some Other Conditions Thereon., J. Hyg. 9:239–48).

The present invention describes that the accumulation of ORNs slows cell replication and is responsible for the lag. Cells lose their lag when the ORNs are extruded out of the cell. Presently, there is no disclosure that teaches that bacteria accumulate ORNs or release them when entering pH neutral environments like those naturally occurring in animal fluids.

Extrusion is induced when cells are exposed to neutral aqueous environments, e.g., saliva, body fluids and physiologic saline. Extrusion can be induced by subjecting the bacterial populations to repeated dilutions or washings, as many as 6, in pH neutral buffers of sufficient molarity to offset the efflux of H+ that accompany the ORNs. Extrusion begins immediately when the cells encounter a pH neutral environment.

Through co-evolution, the immune system has adapted an alert response to the presence of ORNs, learning that their appearance reflects the restarting of exponential growth by the bacteria and the likelihood of an ensuing infection. The inventors discovered that feeding or injecting ORNs smaller than 10 kDa protects mice against the lethality of a subsequent challenge of endotoxin. ORNs released by harmless as well as pathogenic bacteria are effective and appear to be nontoxic. Protection of all the mice is afforded only if the ORNs are administered 32–96 hours before the lethal injection of endotoxin.

The present invention teaches that this phenomenon is the molecular mode of action of the health benefits observed from feeding harmless bacteria in the form of probiotics or fermented dairy products. Numerous clinical trials have been conducted to support the theory first proposed by Elie Metchnikoff in 1917 with mixed results. Trials in which yogurts were consumed have led to more successful results against viruses, bacteria and protozoa than those in which purified isolates were fed. The inventor asserts that the explanation for this difference is that probiotic bacteria are washed before feeding, thereby losing the benefits of the accumulated ORNs. (For examples see: Yolken R. H., Saavedra J. M., Bauman N. A., Oung I., Perman J. A., 1994 Feeding of *B. bifidum* and *S. thermophilus* to infants in hospital for prevention of diarrhoea and shedding of rotavirus. Lancet 344:1046–9 and Hilton, E., Isenberg, H. D., Alperstein, P., France, K., Borenstein, M. T., 1992. Ingestion of Yogurt Containing *L. acidophilus* as Prophylaxis for Candidal Vaginitis. Ann. Inter. Med. 116: 353–7 and Meydani S. N., Ha W-K. Immunologic effects of yogurt. Am J Clin Nutr 2000, 71:861–72).

Before permitting health claims the Food and Drug Administration requires a research-based explanation of the molecular and cellular mode of action of the product. The current invention suggests that the learned response adapted through co-evolution to the release of ORNs meets the Agency's requirement.

The composition of the invention may be administered orally, parenterally, topically, or intranasally to stimulate the immune system by: (1) activating macrophages to release cytokines, in particular IL-1, IL-6 and TNF required to initiate an immune response to prevent or reduce infection, (2) by counteracting the potential pathologic role of macrophages in over-stimulating the inflammatory response locally (for example rheumatoid arthritis and other autoimmune diseases) or systemically (for example septic shock), and (3) by rescuing monocytes from apoptosis.

Circulating monocytes lose viability after 24 hours via apoptosis when cultured in the absence of a stimulus. The administration of ORNs has been found to extend the life of the monocyte population from 24 hours to 72 hours, thereby allowing them to mature into macrophages and extend their ability to fight virulent infections.

The methods of obtaining the composition of the invention comprise growing a selected bacteria in a media outside of the animal to a selected level of enumeration, stressing the selected bacteria thereby initiating the release of stress response factors and thereafter, collecting the supernatant containing the stress response factors. Preferably the stressing of the selected bacteria to induce the release of stress response factors is accomplished by exposing them to environments of neutral pH and reduced levels of nutrients. Most preferably this is accomplished by one or more of the following methods after propagating bacteria to the selected level of enumeration. (1) removing the bacteria from the media by centrifugation and suspending the bacteria in a non-nutritive neutral buffer; (2) adding effective antibiotics to preparations of sensitive bacteria; (3) adding additional bacteria to the media; (4) reducing the volume of the media; (5) removing nutrients from the media; (6) increasing the pH of the media to neutral; and (7) diluting the bacterial broth one-thousand fold with pH neutral buffer.

The life cycle of bacteria encompasses a pre-growth phase (lag), a growth phase in which division greatly exceed death (log), a phase in which growth rates approximate death rates (stationary), and a decline phase in which death greatly exceeds growth (death phase). Strains in their death phases are not reliable sources of strong ORNs. It has now been found that the method of stressing the bacteria is most preferably performed by removing the bacteria from their media while in their late growth phase or stationary phase (about $10^{8-9}$ viable CFUs per ml) and resuspending them at the same cell density in a non-nutritive phosphate buffer at pH 7.6 for sequential stresses of periods of 10–20 minutes at 37°–41° C. The non-nutritive phosphate buffer is preferably phosphate buffered saline (PBS) which is representative of animal secretions, e.g. saliva. Even stronger ORNs are produced by growing feral strains to their stationary phase on agar, or in broth at their optimum temperatures for growth.

Sequential stressing can be performed in a number of ways. A convenient means of sequential stressing is to transfer the bacteria from their growth medium into fresh PBS. This transfer is marked by the immediate release of ORNs. Transferring the bacteria into fresh PBS again induces the release of additional ORNs. A preferred method is to employ endotoxin-free, phosphate-buffer-saline at pH 7.6 in sequential dilutions to mimic physiologic conditions: the dynamic action of bathing and transporting foreign bacteria in body fluids.

The appearance of these factors can be followed by monitoring absorbencies in the ultraviolet, at 220 and preferably at 254 nm. It was discovered that supernatants containing ORNs with a molecular weight greater than 10 kDa were toxic when administered parenterally to mice, so in a preferred embodiment the invention comprises removing all substances greater than 10 kDa by means such as filtration. Thus the supernatant may be filtered so that all ORNs greater than 10 kDa are removed and those of a size less than 10 kDa are retained in solution.

The amount of total ORNs released depends on: (a) the level of bacteria; an optimum level is $5 \times 10^8$ to $3 \times 10^9$ CFUs per ml; at higher levels, fewer ORNs are released per cell; (b) the timing of stress; it has now been found that more potent ORNs are produced by transferring bacteria from their stationary phase in rich media into a non-nutritive buffer; (c) strains selected from the wild provide more ORNs than laboratory strains; however, stressing laboratory strains and repropagating them results in growth rates and the accumulation of ORNs similar to feral strains, (d) the pH of the release solution; pH values at 4.8 induce the release of approximately one-fourth the level of ORNs released at pH 7.6; (e) the temperature; release can be observed at 40° C., and stronger ORNs are produced by bacteria propagated at temperatures less than 37° C., e.g. at 22–32° C.; (f) the time; while release begins immediately, it has now been discovered that short sequential periods of stress of 5 to 20 minutes produce more potent ORNs. The molarity and ionic strengths of the releasing solution appear to be of minor significance in the release of ORNs inasmuch as the internal osmolalities of stationary phase bacteria are 50–100 atmospheres—a level which is unachievable in ordinary buffers.

Generally, for accumulation of the composition of the invention, the ORN-containing supernatant is rendered bacteria-free by filtering through a 0.22 μm filter to yield a sterile preparation containing all sizes of ORNs. Typically, the total ORN fraction consists of 5–20% polymers larger than 30 kDa, 0.2–20% oligomers between 0.5 and 10 kDa and 0.5–95% monomers less than 0.5 kDa in size. The oligomeric fraction between 0.5 and 10 kDa is non-toxic, readily absorbable, activates macrophages, and extends the viability of monocytes. Daily injections of a protective dose of <10 kDa ORNs for five consecutive days does not cause apparent toxicity in mice, i.e. cessation of eating, ruffled fur, huddling, or diarrhea.

Since the ultraviolet spectrum of the composite of ORNs indicates a maximum of 254 nm, the absorbancy at 254 nm can be used to monitor their release. One Arbitrary Unit (AU) of ORNs was established as that level providing an optical density of 0.001 through 1 cm. of a solution.

ORNs from 15 strains of animal-associated, Gram-positive and Gram-negative, aerobic and anaerobic bacteria representing both harmless and virulent pathogens release ORNs as evidenced by the rise in A-254 during stress induced by nutrient reduction at neutral pH. However, the distribution of sizes within 0.5–10 kDa was not equal across all strains.

This invention teaches the selection of organisms and the conditions employed to stress them to yield a maximum level of immuno potent ORNs, preferably between 0.5 and 3 kDa.

This invention teaches the improvement of two natural conditions: the consumption of food by humans or feedstuffs by livestock, which are rich in microbial populations. Pasteurized fresh milk contains less than $10^4$ CFU of bacteria per ml. Fermented dairy products (such as milk, yogurts, and cheeses) typically contain $10^{6-8}$ CFUs per ml of populations of harmless bacteria in stationery phase. When transferred by eating into a nutrient poor environment of neutral pH, the mouth, ORNs are released at corresponding levels. It is this which the present invention explains the frequently reported observations regarding immune stimulation and the benefits derived from consuming fermented foods.

Fresh vegetables containing high levels of harmless bacteria will also stimulate local macrophages and extend the viability of monocytes by releasing ORNs during eating.

If the dwell-time in the mouth can be increased by gelling or thickening agents being applied to the food, the release of ORNs and delivery to oropharyngeal macrophages can be increased to immune-stimulating levels.

Similarly, the practice of administering oral preparations of $10^{8-10}$ CFUs of harmless viable bacteria to livestock to reduce the incidence of infections during shipping and weaning results in the release of ORNs by bacteria lyophilized from rich media. Superior products can be formulated by selecting bacteria and the number of sequential stressors that release a predominance of immuno potent ORNs, 0.5 to 3 kDa in sterile formulations that prolong dwell-time in the mouth. Likewise, the use of gels of pH >5 for the feeding of livestock would induce the slow release of ORNs from the bacteria during product shipment and storage so that at the time of oral introduction into livestock, the maximum level of ORNs would be immediately available.

In addition, these preparations can contain added sterile ORNs to increase their immune stimulating effectiveness. Furthermore, probiotic preparations can be delivered bacteria-free by separating and packaging the active fraction, ORNs.

Additionally, bacterial inoculants of $10^{8-10}$ CFUs per gram of bacteria are commonly added to stored grains and crops to assist and speed the fermentation of plant materials into readily available nutrients for livestock. Presently, strains are selected for their ability to propagate rapidly on the targeted grains and crops. The "probiotic" effect of enhancing the animal's resistance to infection which is often observed from consuming inoculated grains and silages is due to the stimulation of macrophages by ORNs released when these bacteria are introduced into the nutrient-poor, pH neutral environment of the animal's mouth. The probiotic effectiveness of crop inoculants can be increased by selecting strains specific to certain crops plus having the capability to release significant levels of readily-absorbable, non-toxic ORNs as taught herein.

The generation of ORNs is not to be confused with the generation of shock proteins by bacteria resulting from changes in temperature or other conditions. Shock proteins have a molecular weight greater than 10 kDa (typically 30–150 kDa) and their release is not associated with loss of viability. They represent increased synthesis of certain proteins plus the de novo synthesis of new proteins.

Injected bacterial oligodeoxynucleotides (ODN) containing CpG sequences of DNA have been shown to stimulate the immune system of mice to clear pathogens from internal organs. However, the mice must have been grown under sterile conditions and high doses of ODNs were found to be toxic and increase the animal's sensitivity to endotoxin and cause septic shock. In addition, when fed they cause inflammation in the lower respiratory tract. They lack a rational base since consumed bacteria do not release DNA or its components. (See: Tokunaga, T. et al. 1984 Antitumor activity of DNA fraction from *Mycobacterium bovis* BCG: Isolation, physicochemncial characterization and anti-tumor activity J. Nat'l Cancer Inst 72: 955–62, and Kreig, A. M., Love-Homan, L., Yi, A-K. and Harty, J. T. 1998 CpG DNA Induces Sustained IL-12 Expression in Vivo and Resistance to *L. Monocytogenes* Challenge J. Immunol. 161:2428–34, and Sparwasser, T., Miethke, G., Lipford, K Borschert, H Hacker, K Wagner, H 1997 Bacterial DNA causes septic shock Nature 386:336–43 and Schwartz, D Quinn, T Thorne, P Sayeed, S Yi, A-K Kreig, A 1997 CpG motifs in bacterial DNA cause inflammation in the lower respiratory tract J. Clin. Invest. 100:68–75).

In an earlier U.S. Pat. No. 5,840,318, before the present invention in which the inventor determined the chemical nature of the accumulated molecules, the ORNs were referred to as "stress response factors, SRFs." In U.S. Pat. No. 6,589,771 B1, the invention teaches that ORNs are responsible for the lag period of bacteria and further accumulation with time allows bacteria to extend their lag phase into a state of dormancy in which it is resistant to pasteurization. The forced release of ORNs by repeated washings in pH neutral buffers mimics the natural phenomenon of a dormant cell entering a growth-supporting environment and restarting exponential growth. Release also induces the cell into a state of hypermutation marked by a dramatic change in colony morphology and sensitivity to antibiotics.

Spores created by the spore-forming genera including but not limited to, *Bacillus, Clostridium*, and *Sporosarcina*, represent 100% of the vegetative population. In contrast, the present invention has found that only approximately 1% of the populations of bacteria classified as non-spore formers successfully enter and exit the dormant state. If the complexing of ORNs with DNA is properly done, dormancy is reversible but, if executed improperly, which appears to happen in 99% of the populations, the complex is irreversible and the cell is dead; it cannot restart replication. However, 1% of a bacterial population is sufficient to ensure immortality of that species.

Thus the present invention teaches that bacteria release ORNs upon exposure to pH neutral buffers, including saliva and other physiologic fluids. Through co-evolution the immune system has adapted an alert response to the sudden appearance of ORNs. Feeding ORNs to mice 36 hours prior to a lethal injection of endotoxin protected them from death. The ORNs released during the first and second washes, especially the second, appear to have the greatest efficacy in the mouse and in the macrophage assays. Extensive washings trigger the cell to become hypermutative. The inventor observed no side effects from feeding or repeated injections of sterile ORNs; both harmless and harmful bacteria release protective ORNs.

The present invention thus teaches the previously unknown effect that serial washes in acidic buffers do not induce the release of ORNs and do not trigger the reversion of dormant bacteria to their vegetative reproducing forms. The osmolality within the cell is so high that neutral and basic pH becomes the overriding factors inducing the release of ORNs, not the osmolality of the buffer.

Therefore, the above results of the present invention teach how the feeding or injecting of sterile preparations of ORNs can help prevent infections and the onset of toxic shock. Further, elucidation of the mechanisms of their release from the bacteria used to prepare yogurts also provides new insight into the explanation for the health benefits derived from eating fermented foods.

Additionally, for more information about Applicant's invention, one may reference the book, "The Molecular Naturalist", published by the inventor which details the reaction by colleagues to the concepts of the invention and the commercial implications of the invention in the age of Bio terrorism.

Additional objectives and advantages of the invention are set forth in part in the description, and in part will be obvious from the examples, or may be learned by the practice of the invention. The objectives and advantages of the invention will be obtained by means of the instrumentalities and combinations, particularly pointed out in the claims of the invention.

All publications, patents and patent applications identified herein are incorporated by reference, as though set forth herein in full. The invention being thus described, it will be apparent to those skilled in the art that the same may be varied in many ways without departing from the spirit and scope of the invention. Such variations are included within the scope of the following claims.

EXAMPLES

The harmless bacteria, *Lactobacillus acidophilus*, *L. caseii*, and *L. plantarum* were grown in MRS broth (Mann-Rogosa-Sharpe). The pathogen, *Listeria monocytogenes* was grown in BHI broth (Brain Heart Infusion). All cultures were grown at 37° C. without shaking into their stationary phases and enumerated by the most probable numbers method of dilution and plating on MRS or BHI agar, respectively.

Broths were microfuged and the pellets suspended in endotoxin-free 0.1M phosphate buffered saline pH 7.3 (PBS). For serial washings of 20 minutes, the PBS was microfuged and the pellet resuspended in PBS for an additional period of 20 minutes.

To remove the bacteria and molecules larger than 10 kDa, the PBS solutions were first passed through a 0.22 mμ filter and then through a membrane having a cutoff of 10 kDa (Centriplus® 10, Millipore, Medford, Mass.).

The mice were 5–7 week old, female mice (Taconic Farms, N.Y.). The drinking water was autoclaved twice before the bacteria-free preparations of ORNs were added. Forced feeding was via a syringe into the animal's mouth, not stomach.

The endotoxin was derived from *E. coli* 0188:B7 (Sigma St. Louis, Mo.).

Example 1

An i.p. Injection of ≧200 μg of Endotoxin is Lethal to Mice

Mice were injected with 0.2 mL of endotoxin in phosphate buffered saline and became ill within 2 hr and died within 24 hr. To minimize suffering moribund mice were sacrificed. The probabilities were determined by the Chi-square test. The same lethality of this endotoxin was found by Beutler B., Milsark I. W., and Cerami A. C., 1985 Passive immunization against cachectin/tumor necrosis factor protects mice from lethal effect of endotoxin. Science 229:869–71.

TABLE 1

| Dose | Alive | Dead | Prob. |
| --- | --- | --- | --- |
| 400 μg | 0 | 6 | 0.001 |
| 300 | 0 | 6 | 0.001 |
| 200 | 0 | 6 | 0.001 |
| 100 | 4 | 2 | 0.05 |
| Buffer | 6 | 0 | |

Example 2

The Ad Libidum Consumption of Water Containing Sterile ORNs Protected Mice against the Lethality of Endotoxin Mice received an i.p. injection of 400 μg of endotoxin after 3 days of consuming water ad libitum, which contained ORNs released during a single exposure of individual bacterial cultures to PBS for 16 hr. One mL of the drinking water contained <10 kDa ORNs released by 10e9 CFU of bacteria.

TABLE 2

| | Alive | Dead | Prob. |
| --- | --- | --- | --- |
| *L. monocytogenes* | 7 | 1 | >0.01 |
| Control | 0 | 6 | |
| *L. plantarum* | 4 | 2 | >0.10 |
| Control | 0 | 6 | |
| *L. caseii* | 6 | 16 | 0.20 |
| Control | 0 | 12 | |
| *L. acidophilus* | 6 | 14 | 0.20 |
| Control | 0 | 12 | |

Chi-square test. Controls were PBS.

Example 3

Mice are Protected from Endotoxic Death by a Single Injection of PBS Containing <10 kDa ORNs Released by Both Harmless and Pathogenic Bacteria To demonstrate the effectiveness of a single injection of <10 kDa ORNs, mice were injected i.p. with 0.2 mL of a sterile preparation of <10 kDa ORNs released during a single 16 hr exposure to PBS by 10e9 CFU/mL of bacteria followed by a single injection of 400 µg of endotoxin 48 hr later.

ORNs from rapidly growing strains are more protective than slow-growing ones.

Feral bacteria have more ribosomes than lab strains and therefore have a greater potential to accumulate ORNs. *L. monocytogenes* and *L. plantarum* were feral strains and 10e9 CFU/mL were more protective than equal populations of the slower growing lab strains of *L. caseii, L. acidophilus* and *L. fermentum*.

TABLE 3

|  | Alive | Dead | Prob. |
|---|---|---|---|
| *L. monocytogenes* | 9 | 0 | >0.0005 |
| Control | 0 | 9 |  |
| *L. plantarum* | 4 | 1 | >0.10 |
| Control | 0 | 5 |  |
| *L. caseii* | 2 | 4 |  |
| Control | 0 | 6 |  |
| *L. acidophilus* | 1 | 9 |  |
| Control | 0 | 8 |  |
| *L. fermentum* | 0 | 3 |  |
| Control | 0 | 3 |  |

Example 4

A Dose Response Relationship Exists between the Amount of <10 kDa ORNs Consumed and Protection against Endotoxic Death Ad libitum consumption of ORNs released by a single 16 hr exposure of *L. caseii* afforded more protection than a 10:1 dilution against the lethality of injecting 400 µg of endotoxin.

TABLE 4

|  | Alive | Dead | Prob. |
|---|---|---|---|
| From 1 × 10e9 *L. caseii* | 6 | 6 | >0.20 |
| A 10:1 dilution | 1 | 8 |  |
| Control | 0 | 5 |  |

Example 5

ORNs Larger than 10 kDa are not Protective

To demonstrate the difference in effectiveness of ORNs >10 kDa with those <10 kDA, 0.2 mL of preparations of each released by 10e9 CFU/mL of *L. monocytogenes* during a single 16 hr exposure were injected once into mice 48 hr prior to a lethal injection of 400 g of endotoxin.

TABLE 5

|  | Alive | Dead | Prob. |
|---|---|---|---|
| ORNs < 10 kDa | 4 | 0 | >0.05 |
| ORNs > 10 kDa | 0 | 4 |  |
| Control | 0 | 4 |  |

Example 6

A single effective feeding dose for a 25 g mouse is approximately 3 µg of ORNs or 120 µg per kg. By extrapolation, a protective dose for an adult human would be 10 mg or the amount of ORNs one would expect to consume in eating 6 oz of a fermented dairy product like yogurt containing 10e9 CFUs per ml.

To demonstrate the effectiveness of a single forced feeding of ORNs<10 kDa, mice were fed 50 µL of sterile ORNs released during the first (A), second (B) or third (C) serial wash of 20 min duration each, 48 hr before a lethal injection of 400 µg of endotoxin. An aliquot of 50 µL represents the ORNs released by 10e7 CFU of bacteria which contain approximately 3 µg of ORNs by extrapolation (see Physiology of the Bacterial Cell, Neidhardt, F. C., Ingraham, J. L., and Schaechter, M., Sinauer Assoc., Sundrland, Mass., 1990 p 14).

TABLE 6

|  |  | Alive | Dead | Prob. |
|---|---|---|---|---|
| *L. monocytogenes* | A | 6 | 3 | >0.20 |
|  | B | 6 | 3 | >0.20 |
|  | C | 0 | 6 |  |
| Control |  | 0 | 6 |  |
| *L. plantarum* | A | 0 | 3 | >0.15 |
|  | B | 4 | 2 |  |
|  | C | 0 | 6 |  |
| Control |  | 0 | 4 |  |
| *L. caseii* | A | 1 | 3 |  |
|  | B | 0 | 4 |  |
|  | C | 0 | 3 |  |
| Control |  | 0 | 4 |  |

Example 7

ORNs Released by Heat-Killed Bacteria Activate Human Monocytes in Cell Culture but do not Protect Mice against Endotoxic Death To determine the effectiveness of ORNs released by heat-killed bacteria, broths containing $10^8$ CFUs/mL of *L monocytogenes* were heated to 100° C. for 40 min. The PBS-ORNs were collected from the dead culture after its exposure to PBS for 16 hr. The <10 kDa ORNs stimulated monocytes but did not protect mice for a lethal injection of endotoxin. Monocytes at a concentration of 125,000 per well were treated with 10 µL of a 1:1000 dilution of the same preparation of ORNs. Probability was determined by the t test.

The test was an adaptation of Mangan D F, Welch G R, Wahl S M. 1991 Lipopolysaccharide, tumor necrosis factor-α, and IL-1B prevent programmed cell death (apoptosis) in human peripheral blood monocytes J Immunol 146:1541–6.

TABLE 7

|  | Mice | | | Monocytes | |
|---|---|---|---|---|---|
|  | Alive | Dead | Prob | Activated | Prob |
| <10 kDa ORNs from live bacteria | 4 | 1 | >0.1 | 61% | >0.10 |
| <10 kDa ORNs from dead bacteria | 0 | 4 |  | 67% | >0.10 |
| Control | 0 | 3 |  | 10% |  |

Example 8

Mice produced higher levels of IgG against the melanoma antibody MUC-1 when injected three times at one-week intervals with 5 µg of MUC-1 plus 50 µL of sterile <10 kDa SRF released during the first 20 min exposure (A) to PBS, pH 7.3 of *L. monocytogenes* at 10e9 CFU/mL. Control was MUC-1 alone.

Pathogen free (Balb/C X C57BL/6) F1 mice, 6 weeks of age were obtained from The Jackson Lab and immunized subcutaneously over the lower abdomen three times at one week intervals with MUC1-KLH and GD3-KLH containing 5 μg of MUC1 and 5 μg of GD3 plus 50 μL of a sterile preparation of ORNs<10 kDa. MUC1 is a peptide surface antigen associated with human melanoma cells, which was covalently attached to the immunogenic carrier molecule, keyhole limpet hemocyanin (KLH). A fourth booster immunization was given during week 8. Mice were bled prior to the initial vaccination, 7 days after the third vaccination and 7 days after the fourth vaccination. The ELISA assay was performed as described: MUC1 peptide in 0.1 M carbonate buffer pH 11 was coated on ELISA plates at 0.1–0.2 μg per well. Serially diluted antiserum was added to each well and alkaline phosphatase-conjugated goat anti-mouse IgG or anti-mouse IgM was added at a dilution of 1:200 (Southern Biotech Assoc, Inc., Birmingham, Ala.). ELISA titer is defined as the highest dilution yielding an absorbance of 0.1 or greater over that of normal mouse control sera.

TABLE 8

| | Reciprocal of Titer | |
|---|---|---|
| Week | Control Animals | Treated Animals |
| 1 | 580 | 1280 |
| 2 | 1780 | 12320 |
| 3 | 1780 | 4840 |
| 7 | 1040 | 4800 |
| 8 | 1780 | 6800 |

Example 9

Bacteria became hypermutative after 6 serial washes in PBS. On agar the hypermutative population presented polymorphic morphologies and in the disk assay, increased susceptibility to Kanamycin® and Polymixin B®.

The disk diffusion assay was used to determine the susceptibility of vegetative forms of *L. monocytogenes*, before and after 6 serial 20-min washes in PBS. (See Bauer, A, Kirby, W, Sherris, J, Turck, M, 1966 Antibiotic Susceptibility Testing by a Standardize Single Disk Method, Amer J Clin Path 36:41–44).

TABLE 9

| | Diameter of Zone of Inhibition | |
|---|---|---|
| Antimicrobial | Before Washing | After 6 Washes |
| Ampicillin, 10 μg | 32 mm (3.8) | 30 mm (3.6) |
| Kanamycin, 30 μg | 11 (2.66) | 18* (1.97) |
| Polymixin B, 300 IU | 0 | 11** (3.25) |
| Tetracycline, 30 μg | 40 (5.0) | 45 (6.3) |
| Vancomycin, 30 μg | 25 (3.7) | 30 (4.2) |

Data are averages of 6 experiments.
SD are in parentheses.
Data marked with asterisks are significantly different from corresponding data.
**P > 0.0025 as determined by the t test for comparing 2 means.

Example 10

High Pressure Liquid Chromatography (HPLC) of ORNs <10 kDa Reference FIG. 2

FIG. 2 displays a chromatogram of the separation of the <10 kDa ORNs released over a 12 hr period by *L. monocytogenes*. It shows 7 major components, 4 hydrophilic and 3 hydrophobic.

The column was 250 mm×4.6 mm and packed with RP 315 by the manufacturer, BioRad. The first solvent used was aqueous, 0.1% trifluoro-acetic acid, which eluted the group of hydrophilic ORNs between 7 and 11 min. A second solvent was then applied to elute the group of hydrophobic ORNs. It was a progressive solvent beginning with 0% Methyl Cyanide and 0.1% trifluoro-acetic acid and ending after 55 min with 80% Methyl Cyanide and 0.1% trifluoro-acetic acid.

The hydrophilic group consists of 4 major components (labeled "3, 4, 5, and 6") and eluted between 7 and 11 min by 0.1% trifluoro-acetic acid in water. The hydrophobic group consists of 3 major components (labeled "20, 21, and 22") eluted between 38 and 40 min by an aqueous solvent of about 48% Methyl Cyanide and 0.1% trifluoro-acetic acid. Numerous smaller peaks can be observed in the tracing.

The detector was absorbance at 220 nm. Aliquots of both hydrophilic and hydrophobic groups showed UV maxima at 254 nm.

Example 11

Standards and fractions collected from chromatography on Sephadex G-10 of <10 kDa ORNs released by *L. monocytogenes* as shown in FIG. 1 were analyzed by thin layer chromatography. From a standard of known uracil chromatographed on Sephadex G-10 and on thin layer chromatography (shown below), Peak III was judged to be free uracil. Peak I contains the mixture of approximately 6 hydrophobic ORNs. Peak II contains ORNs that are approximately 3–5 nucleotides. Peak IV contains ORNs that are mono and dinucleotides. Free thymine was not found suggesting the absence of products of hydrolyzed DNA, which was expected since washing in PBS did not result in a significant number of deaths in the bacterial population.

$R_f$ values are the quotient of the distance that a substance migrates divided by the distance traveled by the solvent. Their values are determined by the relative solubilities in the solvents used. In general, the larger oligonucleotides are less soluble and have corresponding lower $R_f$ values.

TABLE 10

| | $R_F$ Values | |
|---|---|---|
| Plates pre-coated with: | Silica | Cellulose |
| Peak I | 0.0–0.1 | 0–.23 |
| Peak II | .44 | |
| Peak III | .58 | .58 |
| Peak IV | .47 | |
| Adenine | | .23 |
| Cytosine | .57 | .35 |
| Guanine | .62 | .13 |
| Thymine | .62 | .72 |
| Uracil | .60 | .60 |
| Adenosine | .80 | .26 |
| Cytidine | .58 | .34 |
| Guanosine | .59 | .225 |
| Thymidine | | .69 |
| Uridine | .58 | .57 |
| AMP | .15 | |
| CAMP | .62 | |
| CMP | .09 | |
| GMP | .07 | |
| UMP | .07 | |
| UTP | .05 | |
| TTP | .141 | |

The solvent used to develop the ORNs on pre-coated silica G-25 plates (EM Science) was 2-propanol:concentrated ammonium:water (6:3:1) as recommended by Scheit, K–H., 1967; Silcagel-Dunnschichtchromatographie von Nucleosiden, Nucleotiden und Oligonucleotiden Biochim., Biophys. Acta 134:217–20. The solvent migrated 8–10 cm up the plate over 2 hrs. After drying it was viewed under a UV lamp emitting rays at 254 nm; a duplicate plate was charred with sulfuric acid to expose all compounds. The spots observed under the UV lamp corresponded to those seen by charring.

The solvent to develop the ORNs on pre-coated cellulose plates (EM Science) was isopropanol:concentrated hydrochoric acid:water (65:16.7:18.3) recommended by Grippo, P., M. Iaccarino, M. Rossi, and E. Scarano 1965; Thin-layer chromatography of nucleotides, nucleosides and nucleic acid bases. Biochim. Biophys. Acta 65:95: 1–7. The solvent migrated 8–10 cm up the plate over 2 hr. After drying the plate was viewed under a short wave UV lamp at 254 nm, and a duplicate plate charred with sulfuric acid to expose spots of organic nature. The spots absorbing the UV light were the only ones seen by charring.

Example 12

Using Synthetic ORNs<10 kDa with Structures Specific to Microbes to Stimulate the Immune System The following ORN corresponding to the stimulating ODN, which contain CpG (See Kreig, A M, et al., 1995, CpG Motifs in Bacterial DNA Trigger Direct B-cell Activation, Nature 374: 546–9 and Kreig, A. M., Love-Homan, L., Yi, Ae-Kyung, Harty, J. T., 1995, CpG DNA Induces Sustained IL-12 Expression in Vivo and Resistance to *L. monocytogenes* Challenge, J Immun. 161:2428–34) can be made synthetically and fed to animals at a level of approximately 0.120 mg per kg of body weight for immune stimulation and modulation and protection against microbial invasions and the lethality of endotoxemia.

The base uracil is substituted for thymine yielding:

(AGAGGGUCGCACGCGGUA), SEQ ID NO: 1

(CGUACUGCAACUCG), SEQ ID NO: 2

(AGGUACAGCCAGGACUACGA, SEQ ID NO: 3 and others 0.3 kDa–10 kDa.

Example 13

Using Synthetic Signature Sequences, ORNs<10 kDa, with Structures Specific to Microbes Sequences of oligoribonucleotides <10 kDa which occur specifically in the ribosomes of certain orders, families, genera and species of bacteria can be synthesized and fed to animals at a level of approximately 0.120 mg per kg of body weight for immune stimulation and modulation and protection against microbial invasions and the lethality of endotoxemia. These sequences are documented in a number of publicly accessible data sets, see Zhang, K., Willson, R. C., and Fox, G. E., 2002, Bioinformatics 18(2):244–50 Identification of characteristic oligonucleotides in the bacterial 16S ribosomal RNA dataset.

---

What is claimed is:

1. A composition for stimulating the immune system of an animal comprising oligonucleotides (ORNs) from bacteria, each ORN having a molecular weight less than 10 kDa, and wherein said oligoribonucleotides (ORNs) occur only in microbes or at higher frequencies than in mammals, and consisting of a sequence selected from the group consisting of:

(AGAGGGUCGCACGCGGUA), SEQ ID NO: 1

(CGUACUGCAACUCG) SEQ ID NO: 2 and (AGGUACAGCCAGGACUACGA) SEQ ID NO: 3 and a pharmaceutically acceptable carrier or diluent.

2. The composition of claim 1 wherein the higher frequencies of oligoribonucleotides (ORNs) occurring in microbes is at least 10 fold more frequent.

* * * * *